United States Patent [19]

Quinlan

[11] 4,035,412
[45] July 12, 1977

[54] METHYLENE PHOSPHONATES OF POLY-DIEPOXIDIZED POLYALKYLENE POLYAMINES

[75] Inventor: Patrick M. Quinlan, Webster Groves, Mo.

[73] Assignee: Petrolite Corporation, St. Louis, Mo.

[21] Appl. No.: 148,216

[22] Filed: May 28, 1971

[51] Int. Cl.² .......................................... C07C 9/38
[52] U.S. Cl. ............................. 260/502.5; 210/58; 252/8.55 B; 252/8.8; 252/DIG. 11; 260/340.6; 260/348 R; 260/429 J; 260/438.5 R; 260/439 R; 260/501.12
[58] Field of Search ...................... 260/502.5, 501.12

[56] References Cited

U.S. PATENT DOCUMENTS

| | | | |
|---|---|---|---|
| 2,673,213 | 3/1954 | Bersworth | 260/502.5 |
| 2,673,214 | 3/1954 | Bersworth | 260/502.5 |
| 2,964,549 | 12/1960 | Ramsey et al. | 260/502.5 |
| 3,498,969 | 3/1970 | Lewis | 260/945 |
| 3,549,728 | 12/1970 | Balde et al. | 260/502.5 |

*Primary Examiner*—Joseph E. Evans
*Attorney, Agent, or Firm*—Sidney B. Ring; Hyman F. Glass

[57] ABSTRACT

Methylene phosphonates of poly-diepoxidized polyalkylene polyamines and to uses therefor, particularly as scale inhibitors, chelating agents, etc.

5 Claims, No Drawings

METHYLENE PHOSPHONATES OF POLY-DIEPOXIDIZED POLYALKYLENE POLYAMINES

Most commercial water contains alkaline earth metal cations, such as calcium, barium, magnesium, etc., and anions such as bicarbonate, carbonate, sulfate, oxalate, phosphate, silicate, fluoride, etc. When combinations of these anions and cations are present in concentrations which exceed the solubility of their reaction products, precipitates form until their product solubility concentrations are not longer exceeded. For example, when the concentrations of calcium ion and carbonate ion exceed the solubility of the calcium carbonate reaction product, a solid phase of calcium carbonate will form as a precipitate.

Solubility product concentrations are exceeded for various reasons, such as evaporation of the water phase, change in pH, pressure or temperature, and the introduction if additional ions which can form insoluble compounds with the ions already present in the solution.

As these reaction products precipitate on the surfaces of the water-carrying system, they form scale. The scale prevents effective heat transfer, interferes with fluid flow, facilitates corrosive processes, and harbors bacteria. Scale is an expensive problem in many industrial water systems, causing delays and shutdowns for cleaning and removal.

Scale-forming compounds can be prevented from precipitating by inactivating their cations with chelating of sequestering agents, so that the solubility of their reaction products is not exceeded. Generally, this approach requires many times as much chelating or sequestering agent as cation present, and the use of large amounts of treating agent is seldom desirable or economical.

More than twenty-five years ago it was discovered that certain inorganic polyphosphates would prevent such precipitation when added in amounts far less than the concentrations needed for sequestering or chelating. See, for example, Hatch and Rice, "Industrial Engineering Chemistry," vol. 31, p. 51, at 53; Reitemeier and Buchrer, "Journal of Physical Chemistry," vol. 44, No. 5, p. 535 at 536 (May 1940); Fink and Richardson U.S. Pat. No. 2,358,222; and Hatch U.S. Pat. No. 2,539,305. When a precipitation inhibitor is present in a potentially scaleforming system at a markedly lower concentration than that required for sequestering the scale forming cation, it is said to be present in "threshold" amounts. Generally, sequestering takes place at a weight ratio of threshold active compound to scale-forming cation component of greater than about ten to one, and threshold inhibition generally takes place at a weight ratio of threshold active compound to scale-forming cation component of less than about 0.5 to 1.

The "threshold" concentration range can be demonstrated in the following manner. When a typical scale-forming solution containing the cation of a relatively insoluble compound is added to a solution containing the anion of the relatively insoluble compound and a very small amount of a threshold active inhibitor, the relatively insoluble compound will not precipitate even when its normal equilibrium concentration has been exceeded. If more of the threshold active compound is added, a concentration is reached where turbidity or a precipitate of uncertain composition results. As still more of the threshold active compound is added, the solution again becomes clear.

This is due to the fact that threshold active compounds in high concentrations also act as sequestering agents, although sequestering agents are not necessarily "threshold" compounds. Thus, there is an intermediate zone between the high concentrations at which they act as threshold inhibitors. Therefore, one could also define "threshold" concentrations of the threshold active compounds below that concentration at which this turbid zone or precipitate is formed. Generally the threshold active compound will be used in a weight ratio of the compound to the cation component of the scale-forming salts which does not exceed about 1.

The polyphosphates are generally effective threshold inhibitors for many scale-forming compounds at temperatures below 100° F. But after prolonged periods at higher temperatures, they lose some of their effectiveness. Moreover, in an acid solution, they revert to ineffective or less effective compounds.

A compounds that has sequestering powers does not predictably have threshold inhibiting properties. For example, ethylenediamine tetracetic acid salts are powerful sequesterants but have no threshold activities.

I have now discovered a process for inhibiting scale such as calcium, barium and magnesium carbonate, sulfate, silicate, etc., scale which comprises employing threshold amounts of methylene phosphonates of poly-diepoxidized polyalkylene poly-amines.

The amines employed herein are polyalkylenepolyamines, for example, of the formula

where n is an integer for example 1 to 25 or more, such as 2 - 10, but preferably 2 – 5, etc., and A is an alkylene group —$(CH_2)_m$—where m is 2 – 10 or more, but preferably ethylene or propylene.

One or more of the hydrogens on the $CH_2$ group may be substituted for example, by such groups as alkyl groups, for example, methyl, ethyl, etc. Examples of A include

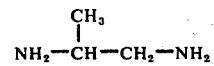

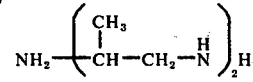

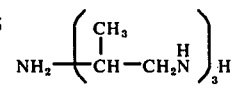

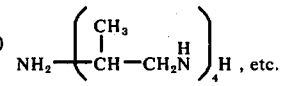

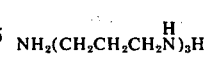

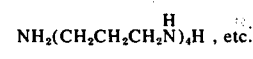

-continued

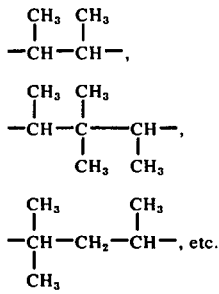

Examples of polyamines include the following: ethylene diamine, diethylene triamine, dipropylene triamine, triethylene tetramine, tripropylene tetramine, tetraethylene pentamine, tetrapropylene pentamine, polyalkyleneimines, i.e., the higher molecular weight amines derived from alkyleneimine such as polyethyleneimines, polypropyleneimines, for example having 50, 100 or more alkylene amino units, etc. Mixtures of the above polyamine amines and those polyamines containing both ethylene and propylene groups, for example

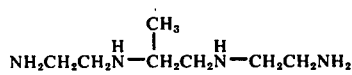

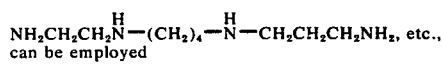
can be employed

These include the following:

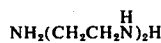

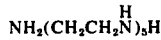

The composition of this invention may be prepared by the following general reactions.

1.
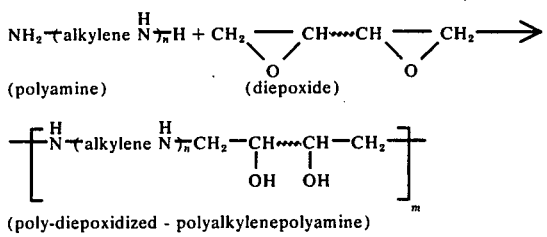

2.
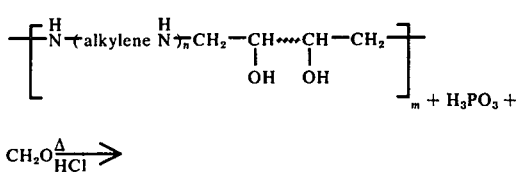

where
  $n = 1-25$ but preferably 1-5
  $m = 1-100$ but preferably 1-10 $M$ = a salt moiety, hydrogen, amine-derived ammonium, ammonium, etc.
  ⁓⁓⁓designates a group joining the two epoxide units The bridge ⁓⁓⁓ between the terminal epoxide groups may vary widely. The following are exemplary. In these formulae —CH$_2$-O-Z-O-CH$_2$— is of the above formulae

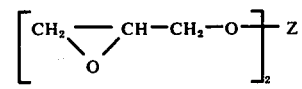

where Z - arylene such as phenylene, substituted phenylene, such as

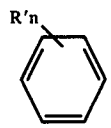

R' is a substituted group such as alkyl, aryl, halo, alkoxy, etc.; where Z is alkarylalkylene such as

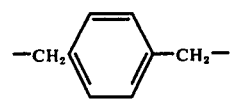

and substituted derivatives; diaryl such as

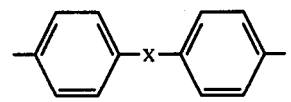

where X is alkylene, alkylene ether,

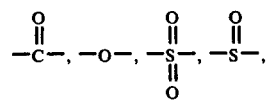

S, etc., or substituted derivatives such as

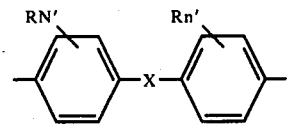

where R' is a substituted group such as alkyl, aryl, halo, alkoxy, etc.; where Z is —(AO)$_n$—A— where A is an alkylene such as ethylene, propylene, butylene, octylene, etc., mixtures thereof, block polymers thereof, etc.; where $n$ is 1 or more such as 1-100, for example 1-50, but preferably 1-10.

In addition the epoxide groups can be bonded directly, i.e., where ⁓⁓⁓ is a valence bond, for example,

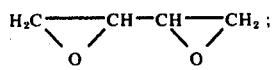

by a hydrocarbon bridge, for example,

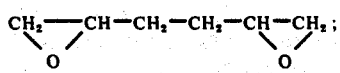

by an alkylene ethylene ether group, i.e., where ~~~ is —CH$_2$-O-CH$_2$—

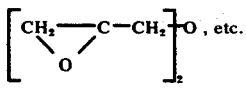

In addition the bridge may be of a more complex structure, such as

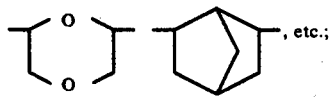

where the epoxide group is part of a ring structure such as

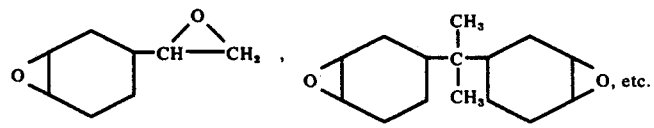

In addition, the epoxide group can be other than an ethylene oxide ring, i.e.,

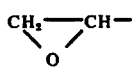

but can also be substituted such as

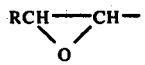

where R is alkyl for example CH$_3$, C$_2$H$_5$, etc.

The poly-diepoxidized polyamine is then phosphomethylolated. This is preferably carried out by the Mannich reaction as illustrated in the following reaction wherein —NH indicates at least one reactive group on the polyamine

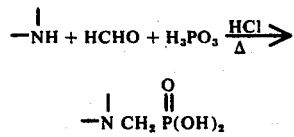

The Mannich reaction is quite exothermic and initial cooling will generally be required. Once the reaction is well under way, heat may be required to maintain refluxing conditions. While the reaction will proceed at temperatures over a wide range, i.e., from 80° to 150° c, it is preferred that the temperatures of the reaction medium be maintained at the refluxing temperatures. The reaction is preferably conducted at atmospheric pressure, although sub-atmospheric and superatmospheric pressures may be utilized if desired. Reaction times will vary, depending upon a number of variables, but the preferred reaction time is 1 to 5 hours, and the most preferred reaction time is 2-½ to 3-½ hours.

Although the phosphonic acid or the formaldehyde may be added in either order, or together to the reaction mixture, it is preferred to add the phosphonic acid to the poly-diepoxidized polyalkylene polyamine and then to slowly add the formaldehyde under refluxing conditions. Generally, about ½ to 10 moles or more of formaldehyde and about ½ to 10 moles or more of phosphonic acid can be used per mole equivalent of amine, although the most preferred molar equivalent ratios of formaldehyde: phosphonic acid: amine is 1:1:1. Excess formaldehyde and/or phosphonic acid function essentially as solvents, and thus there is no real upper limit on the amount of these materials which may be used, per mole equivalent of amine, although such excess amounts naturally add to the cost of the final product and are therefore not preferred. The preferred molar equivalent ratios are ½ to 2 moles each of the formaldehyde and phosphonic acid per mole equivalent of amine.

The Mannich reaction will proceed in the presence or the absence of solvents. The reaction may be carried out as a liquid-phase reaction in the absence of solvents or diluents, but is preferred that the reaction be carried out in an aqueous solution containing from about 40 to about 50% of the reaction monomers. Preferred conditions for the Mannich reaction include the use of formaldehyde based on the molar equivalent amount of the amine compound, the use of a stoichiometric amount of phosphonic acid based on the molar equivalent amount of amine (e.g., on the amine active hydrogen content), refluxing conditions and a pH of less than 2 and preferably less than 1.

Although formaldehyde is preferred, other aldehydes or ketones may be employed in place of formaldehyde such as those of the formula

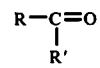

where R + R' are hydrogen, or a hydrocarbon group such as alkyl, i.e., methyl, ethyl, propyl, butyl, etc., aryl, i.e., phenyl, alkylphenyl, phenalkyl, etc. cycloalkyl, i.e., cyclohexyl, etc.

The compound can also be prepared by a modified Mannich reaction by employing a chloromethylene phosphonate

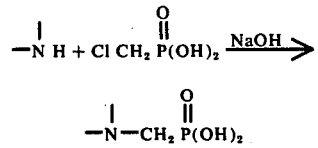

Thus, the compositions of this invention are prepared by 1. diepoxidizing the alkylene polyamine to the desired degree of polymerization while leaving some unreacted NH groups.

2. phosphomethylolating the poly-diepoxidized polyamine so that at least one, or all of the NH groups, or less than all of the groups are phosphomethylolated.

In general it is preferred that at least 50% but preferably at least 80% of the nitrogen-bonded hydrogens of the poly-diepoxided polyamine be replaced by methylene phosphonate groups.

Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 100 ppm and are preferably used in concentrations of less than 25 ppm.

The compounds of the present invention (e.g., the acid form of the compounds) may be readily converted into the corresponding alkali metal, ammonium or alkaline earth metal salts by replacing at least half of the hydrogen ions in the phosphonic acid group with the appropriate ions, such as the potassium ion or ammonium or with alkaline earth metal ions which may be converted into the corresponding sodium salt by the addition of sodium hydroxide. If the pH of the amine compound is adjusted to 7.0 by the addition of caustic soda, about one half of the —OH radicals on the phosphorous atoms will be converted into the sodium salt form.

The scale inhibitors of the present invention illustrate improved inhibiting effect at high temperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 ppm to about 50,000 ppm of scale-forming salts. The compounds of the present invention effectively inhibit scale formation when present in an amount of from 0.1 to about 100 ppm, and preferably 0.2 to 25 ppm wherein the amounts of the inhibitor are based upon the total aqueous system. There does not appear to be a concentration below which the compounds of the present invention are totally ineffective. A very small amount of the scale inhibitor is effective to a correspondingly limited degree, and the threshold effect is obtained with less than 0.1 ppm. There is no reason to believe that this is the minimum effective concentration. The scale inhibitors of the present invention are effective in both brine, such as sea water, and acid solutions.

In the specific examples the general method of phosphomethylolation is that disclosed in Netherlands Pat. Nos. 6407908 and 6505237 and in the Journal of Organic Chemistry, vol. 31, No. 5, 1603–1607 (May, 1966). These references are hereby incorporated by reference.

In general, the method consists of the following: The poly-diepoxidized polyamine is slowly added with cooling to the mixture of phosphonic and hydrochloric acids. After the addition is completed, the reaction mixture is heated to 100°–110° C. and the aqueous formaldehyde is slowly added over a period of 1 to 1-½ hours while maintaining a temperature of 100°–110°. After the addition is completed, the reaction mixture is held at reflux temperatures for 1-2 additional hours. The preferred molar equivalent ratios are ½ – 2 moles each of the formaldehyde and phosphonic acid per mole equivalent of amine, although the most preferred molar equivalent ratios of formaldehyde: phosphonic acid: amine is 1:1:1.

The poly-diepoxidized polyamines suitable as intermediates for the preparation of the methylene phosphonic acids of this invention are prepared by the slow addition of a diepoxide to a hot solution of the polyamine dissolved in water or aqueous alcohol. The addition is terminated short of a point where serious cross linking of the generated polymeric species would occur. When excessive cross linking occurs, an undesirable insoluble resin is formed. The poly-diepoxidized polyamines form viscous solutions which can be further reacted to form methylene phosphonic acids.

In general 1 or less than 1 mole of diepoxide per mole of polyamine is used depending on the desired degree of polymerization.

EXAMPLE 1

To a stirred refluxing solution of 76 g. tetraethylenepentamine in 50 g. of water and 25 g. of t-butyl alcohol was slowly added 10 g. of Dow Chemical epoxy resin DER*-736. At this point, the reaction mixture became quite viscous. The reaction mixture was then held at reflux for one additional hour.

To a solution of 83 g. of phosphorous acid, and 116 g. of concentrated hydrochloric acid, was slowly added with cooling 100 g. of the poly-diepoxidized polyamine described above. The resulting solution was heated to reflux and 89g. of 37% aqueous formaldehyde was added dropwise over a period of one hour. The resulting solution was then held at reflux for an additional two hours. A portion of the product was neutralized with sodium hydroxide.

*DER 736 is the diglycidyl ether of polypropylene glycol. It has an epoxy equivalent weight of 175–205.

EXAMPLE 2

To a stirred refluxing solution of 75 g. triethylenetetramine in 50 g. of water and 25 g. of t-butyl alcohol was slowly added 20 g. of bis (2,3-epoxy-cyclopentyl) ether. During the addition, the reaction mixture became quite viscous. The reaction mixture was then held at reflux for one additional hour.

To a solution of 66 g. off phosphorous acid, and 93 g. of concentrated hydrochloric acid, was slowly added with cooling, 100 g. of the poly-diepoxidized polyamine solution described above. The resulting solution was heated to reflux and 70 g. of 37% aqueous formaldehyde was added dropwise over a period of one hour. The resulting solution was then held at reflux for an additional 2 hours. A portion of the product was neutralized with sodium hydroxide.

EXAMPLE 3

Using the method described in Examples 1 and 2, 75 g. of pentaethylenehexamine was reacted with 23 g. of 1, 4-bis (2,3-epoxypropoxy) butane. 100 g. of a 50% solution of this reaction product was phosphomethylolated with 91 g. of phosphorous acid and 100 g. of 37% aqueous formaldehyde in the presence of 125 g. of concentrated hydrochloric acid.

EXAMPLE 4

Using the method described in Examples 1 and 2, 75 g. of tetraethylenepentamine was reacted with 20 g. of vinyl cyclohexene dioxide. 100 g. of a 50% solution of this reaction product was phosphomethylolated with 83 g. of phosphorous acid and 89 g. of 37% aqueous formaldehyde in the presence of 116 g. of concentrated hydrochloric acid.

EXAMPLE 5

Using the method described in Examples 1 and 2, 75 g. of diethylenetriamine was reacted with 20 g. of 1, 3-bis(2,3-epoxypropoxy) benzene. 100 g. of a 50% solution of this reaction product was phosphome- thylolated with 33 g. of phosphorous acid and 40 g. of 37% aqueous formaldehyde in the presence of 70 g. of concentrated hydrochloric acid.

EXAMPLE 6

Using the method described in Examples 1 and 2, 75 g. of pentaethylenehexamine was reacted with 22 g. of 2, 2-bis (p-(2, 3-epoxypropoxy) phenyl) propane. 100 g. of a 50% solution of this reaction product was phosphomethylolated with 91 g. of phosphorous acid and 100 g. of 37% aqueous formaldehyde in the presence of 125 g. of concentrated hydrochloric acid.

Corresponding poly-diepoxided polyamines are similarly prepared from the diepoxides of Table I and the products thereupon converted to methylene phosphoric acids. The diepoxides used in the above examples have the formulae indicated in Table I.

Table I

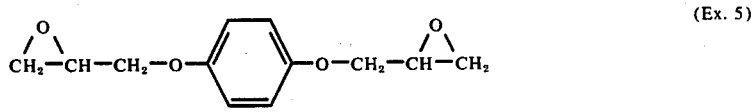 (Ex. 5)

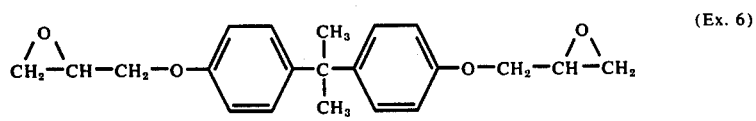 (Ex. 6)

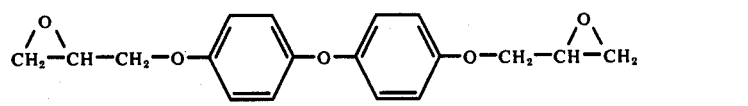

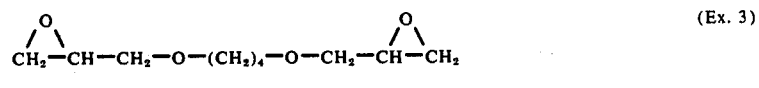 (Ex. 3)

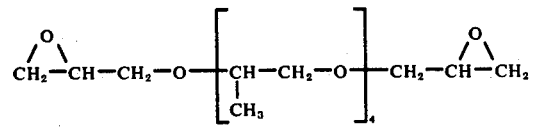 (Ex. 1)

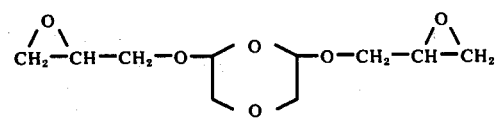

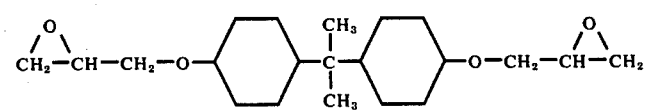

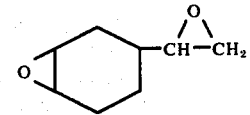 (Ex. 4)

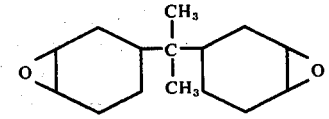

Table I-continued

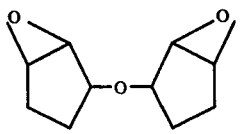
(Ex. 2)

The compounds of this invention may also be prepared in hot, alkaline, aqueous solution by the reaction of chloromethylene phosphonic acid with the oxyalkylated polyamines.

This method has been described by Bersworth in U.S. Pat. No. 2,599,807 and 2,841,611 and by Ramsey in U.S. Pat. No. 2,917,528.

In carrying out the reaction sufficient alkalinity must be present to neutralize the acidity of the chloromethyl phosphonic acid and absorb the hydrochloric acid liberated by the reaction. It is desirable to maintain an excess of the alkaline material, such as sodium hydroxide, to drive the reaction to completion.

One or more or all of the remaining hydrogen atoms on the nitrogen atoms in the poly-diepoxidized polyamines may be replaced with methylene-phosphonic groups depending on the proportions of the oxyalkylated polyamine and the chloromethylene phosphonic acid reactants. Since the reaction products are obtained in the form of salts, depending on the neutralizing base used, they may be converted to the free acids by reaction with inorganic acids or ion exchange resins.

The degree of phosphomethylolation can be controlled by varying the molar ratios of the reactants. However, for effective scale inhibition, I have found that the maximum degree of phosphomethylolation, (100%) is to be preferred. In other words, a complete replacement of the remaining active hydrogen atoms on the poly-diepoxidized alkylene polyamines by methylene phosphonate groups has been found to be most desirable for scale inhibition.

These methylene phosphonates are threshold active scale inhibitors at room temperature, and are also effective at elevated temperatures. They also retain their effectiveness in acid and salt solution and have excellent solubility in waters with high hardness content.

Calcium Scale Inhibition Test

The procedure utilized to determine the effectiveness of my scale inhibitors in regard to calcium scale is as follows:

Several 50 ml. samples of a 0.04 sodium bicarbonate solution are placed in 100 ml. bottles. To these solution is added the inhibitor in various known concentrations. 50 ml. samples of a 0.02 M $CaCl_2$ solution are then added.

A total hardness determination is then made on the 50—50 mixture utilizing the well known Schwarzenbach titration. The samples are placed in a water bath and heated at 180° F. 10 ml. samples are taken from each bottle at 2 and 4 hour periods. These samples are filtered through millipore filters and the total hardness of the filtrates are determined by titration.

$$\frac{\text{Total hardness after heating}}{\text{Total hardness before heating}} \times 100 = \% \text{ inhibition}$$

Table II

| Inhibitor | Salt | Conc. ppm | % Scale Inhibition |
|---|---|---|---|
| Example 1 | H | 50 | 65 |
| " | Na | 50 | 55 |
| " | H | 20 | 55 |
| " | Na | 20 | 45 |
| Example 2 | H | 50 | 68 |
| " | Na | 50 | 57 |
| " | H | 20 | 53 |
| " | Na | 20 | 47 |
| Example 3 | H | 50 | 66 |
| " | Na | 50 | 58 |
| " | H | 20 | 54 |
| " | Na | 20 | 51 |
| Example 4 | H | 50 | 64 |
| " | Na | 50 | 53 |
| " | H | 20 | 55 |
| " | Na | 20 | 48 |
| Example 5 | H | 50 | 58 |
| " | Na | 50 | 57 |
| " | H | 20 | 49 |
| " | Na | 20 | 42 |
| Example 6 | H | 50 | 59 |
| " | Na | 50 | 49 |
| " | H | 20 | 58 |
| " | Na | 20 | 49 |
| Commercial Phosphonate Scale Inhibitor | Na | 50 | 40 |
| Commercial Organic Phosphate Scale Inhibitor | Na | 50 | 35 |

USE IN THE CHELATION OR SEQUESTRATION OF METAL IONS

The chelating or sequestering agents of the present invention are of wide utility such as when it becomes necessary to sequester or inhibit the precipitation of metal cations from aqueous solutions. Among their many uses are the following applications:

Soaps and detergents, textile processing, metal cleaning and scale removal, metal finishing and plating, rubber and plastics, industry, pulp and paper industry, oil-well treatment, chelation in biological systems.

An important function of these compounds is their ability to sequester $Fe^{+2}$. In secondary oil recovery by means of water floods, waters are frequently mixed on the surface prior to injection. Frequently these waters contain amounts of $Fe^{+2}$ and $H_2S$. If these incompatible waters are mixed, An FeS precipitate results which can plug the sand face of the injection well. Another of their functions is to prevent formation of gelatinous iron hydroxides in the well and in the effluent production waters.

To demonstrate the effectiveness of the poly-diepoxidized polyamine methylene phosphonic acids in chelating $Fe^{+2}$, the following test procedure was utilized. Into a flask that contained a known concentration of the sequestering agent, and enough sodium hydroxide or hydrochloric acid to give the desired pH was placed a 100 ml. aqueous sample of ferrous ammonium sulfate (20 ppm of $Fe^{+2}$); after final pH adjustment, the solution was allowed to remain at ambient temperatures for 48 hours. The solution was centrifuged for 1 hour to remove collodial iron hydroxide and an aliquot of the supernatant solution was analyzed by atomic absorption to determine the iron concentration.

The following table illustrates the ability of the sequestering agents of the present invention to sequester $Fe^{+2}$, as compared to the well known sequestering agent tetra-sodium ethylenediamine tetra-acetate (EDTA).

Table III

| pH | Sequestering Agent (ppm) | Amount of Iron Sequestered (ppm) |
|---|---|---|
| | Product Example | |
| 5 | 1 (50) | (19) |
| 5 | 2 (50) | (16) |
| 5 | 3 (50) | (15) |
| 5 | EDTA (50) | ( 7) |
| 7 | 1 (50) | (19) |
| 7 | 2 (50) | (17) |
| 7 | 3 (50) | (12) |
| 7 | EDTA (50) | ( 7) |
| 10 | 1 (150) | (17) |
| 10 | 2 (150) | (14) |
| 10 | 3 (150) | (20) |
| 10 | EDTA (150) | ( 6) |

As one can observe from the preceding table, the sequestering agents of this invention are as effective, and in some cases superior, to EDTA when tested over a wide pH range.

The sequestering agents of this invention are also quite effective in sequestering other metal cations in aqueous solutions. For example, a test was conducted in which 60 ppm of the sequesterant were dissolved in 100 ml. of water. The pH was adjusted to 9 and maintained there. Metal cations were added, in the following amounts, before a noticeable precipitate was formed.

Table IV

| Sequesterant | Metal (ppm) Sequestered per 60 ppm of Sequesterant | |
|---|---|---|
| Product Example 1 | $Fe^{+3}$ | ( 60) |
| Example 1 | $Al^{+3}$ | (100) |
| Example 1 | $Cu^{+2}$ | (120) |
| Example 1 | $Ni^{+2}$ | ( 50) |
| Example 3 | $Fe^{+3}$ | ( 60) |
| Example 3 | $Al^{+3}$ | (100) |
| Example 3 | $Cu^{+2}$ | (120) |
| Example 3 | $Ni^{+3}$ | ( 60) |

Other heavy metals sequestered by the sequestering agents of this invention such as cobalt, manganeses, chromium and the like.

In summary, the products of this invention are poly-diepoxidized, phosphomethylolated polyalkylene polyamines. Diepoxidization is carried out under polymerizing conditions and in general 1 mole or less than 1 mole of diepoxide is added per mole of polyamine so as to minimize crosslinking. The phosphomethylolated groups, i.e.,

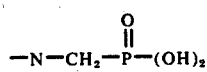

(or salts thereof) preferably comprise at least 50% but preferably 80-100% of the available nitrogen-bonded hydrogens on the poly-diepoxided polyamine. The preferred polyalkylene has 1 – 25 such as 2 – 10 nitrogen units and most preferably 2 – 5 nitrogen units -- the preferred embodiment being polyethylene polyamines. These compositions are employed as scale inhibitors, chelating agents, and the like. Various modifications will be evident to those skilled in the art.

The terms "phosphonic acid" and "phosphorous acid" may be used interchangeably and relate to $H_3PO_3$, i.e.,

We claim:
1. Methylene phosphonates of poly-diepoxidized polyalkylene polyamines having
   1. nitrogen-bonded methylene phosphonate units of the formula $-CH_2PO(OM)_2$ where M is alkali metal, alkaline earth metal, hydrogen, amine-derived ammonium or ammonium,
   2. at least one unit of the formula

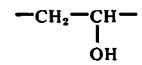

and
   3. at least one unit of the formula

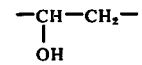

the $-CH_2-$ of the

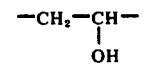

unit (2) being bonded to one terminal nitrogen of the polyalkylene polyamine and the $-CH_2-$ of the

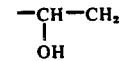

unit (3) being bonded to the other terminal nitrogen of the polyalkylene polyamine, the poly-diepoxidized polyalkylene polyamine being the reaction product of polyalkylene polyamine and diepoxide.

2. The methylene phosphonates of poly-diepoxidized polyalkylene polyamines of claim 1 where the polyalkylene polyamines are polyethylene polyamines.

3. The methylene phosphonates of poly-diepoxidized polyalkylene polyamines of claim 2 where the polyethylene polyamines are of the formula

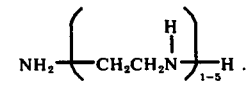

4. The methylene phosphonates of a poly-diepoxidized polyalkylene polyamine having repeating units of the formula

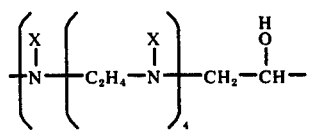

-continued
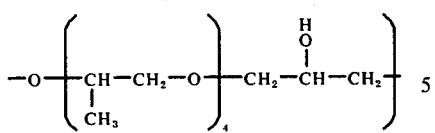
where X is hydrogen or —CH$_2$PO(OM)$_2$ where M is alkali metal, alkaline earth metal, hydrogen, amine-derived ammonium or ammonium and at least 50% of the X units are CH$_2$PO(OM)$_2$.
5. The methylene phosphonates of poly-diepoxidized poly-alkylene polyamines of claim 4 where at least 80% of the X units is —CH$_2$PO(OM)$_2$.
* * * * *